(12) United States Patent
Mathers

(10) Patent No.: US 9,181,142 B2
(45) Date of Patent: Nov. 10, 2015

(54) PLANT BASED MONOMERS AND POLYMERS

(71) Applicant: The Penn State Research Foundation, University Park, PA (US)

(72) Inventor: Robert T. Mathers, Gibsonia, PA (US)

(73) Assignee: The Penn State Research Foundation, University Park, PA (US)

( * ) Notice: Subject to any disclaimer, the term of this patent is extended or adjusted under 35 U.S.C. 154(b) by 262 days.

(21) Appl. No.: 13/859,495

(22) Filed: Apr. 9, 2013

(65) Prior Publication Data

US 2013/0324688 A1    Dec. 5, 2013

Related U.S. Application Data

(60) Provisional application No. 61/654,589, filed on Jun. 1, 2012.

(51) Int. Cl.
| | | |
|---|---|---|
| *C07C 1/213* | (2006.01) | |
| *C07C 67/347* | (2006.01) | |
| *C07C 67/38* | (2006.01) | |
| *C07C 5/25* | (2006.01) | |
| *C08G 69/00* | (2006.01) | |
| *C08G 63/78* | (2006.01) | |
| *C08G 63/00* | (2006.01) | |
| *C07D 307/77* | (2006.01) | |
| *C08F 132/06* | (2006.01) | |
| *C08G 63/137* | (2006.01) | |
| *C08G 63/199* | (2006.01) | |
| *C08G 63/553* | (2006.01) | |
| *C07C 6/04* | (2006.01) | |
| *C08G 69/26* | (2006.01) | |
| *C08G 69/28* | (2006.01) | |

(52) U.S. Cl.
CPC . *C07C 1/213* (2013.01); *C07C 5/25* (2013.01); *C07C 5/2581* (2013.01); *C07C 5/2593* (2013.01); *C07C 6/04* (2013.01); *C07C 67/347* (2013.01); *C07C 67/38* (2013.01); *C07D 307/77* (2013.01); *C08F 132/06* (2013.01); *C08G 63/00* (2013.01); *C08G 63/137* (2013.01); *C08G 63/199* (2013.01); *C08G 63/553* (2013.01); *C08G 63/78* (2013.01); *C08G 69/00* (2013.01); *C08G 69/26* (2013.01); *C08G 69/28* (2013.01); *C07C 2101/14* (2013.01); *C07C 2101/16* (2013.01); *C07C 2103/70* (2013.01); *C07C 2531/22* (2013.01); *C07C 2531/24* (2013.01); *C07C 2531/28* (2013.01)

(58) Field of Classification Search
CPC .... C08F 132/06; C08G 63/00; C08G 63/137; C08G 63/199; C08G 63/553; C08G 63/78; C08G 69/00; C08G 69/26; C08G 69/28; C07C 1/213; C07C 5/25; C07C 5/2581; C07C 5/2593; C07C 6/04; C07C 67/347; C07C 67/38; C07C 2101/14; C07C 2101/16; C07C 2103/70; C07C 2531/22; C07C 2531/24; C07C 2531/28; C07D 307/77

USPC .......... 526/308; 528/307; 549/237; 560/114, 560/118; 564/134, 153; 585/318, 377
See application file for complete search history.

(56) References Cited

U.S. PATENT DOCUMENTS

| | | | | |
|---|---|---|---|---|
| 2,421,876 | A | * | 6/1947 | Gerhart ............................ 525/42 |
| 3,746,695 | A | * | 7/1973 | Ofstead .......................... 526/281 |
| 2010/0094034 | A1 | * | 4/2010 | Kaido et al. .................. 554/145 |

OTHER PUBLICATIONS

Synthesis and Polymerization of Renewable 1,3-Cyclohexadiene Using Metathesis, Isomerization, and Cascade Reactions with Late-metal Catalysts, Mathers et al. , Macromol. Rapid Commun. 2011, 32, 1338-1342.*

Sustainable Methods for the Synthesis and Polymerization of 1,3-Cyclohexadiene From Plant Oils, Mathers et al., Prepr. Pap.-Am. Chem. Soc., Div. Fuel Chem. 2010,55 (1).*

Mialon et al. (Biorenewable polyethylene terephthalate mimics derived from lignin and acetic acid, Green Chem.,vol. 12, No. 10, Oct. 2010, pp. 1677-1872).*

Notice of Transmittal of International Search Report and Written Opinion, International Search Report, and Written Opinion, issued in PCT/US2013/035958, dated Jul. 26, 2013.

International Preliminary Report on Patentability dated Dec. 2, 2014 issued in corresponding International Patent Application No. PCT/US2013/035958.

G. Busca: "Bases and Basic Materials in Chemical and Environmental Processes. Liquid versus Solid Basicity", Chem. Rev., 2010, 110, pp. 2217-2249.

H. Gorzawski, et al.: "Preparation of superbases and their use as catalysts for double-bond isomerization", Journal of Molecular Catalysis A: Chemical 144, 1999, pp. 181-187.

Robert T. Mathers, et al.: "Renewable Chain Transfer Agents for Metallocene Polymerizations: The effects of Chiral Monoterpenes on the Polyolefin Molecular Weight and Isotacticity", Journal of Polymer Science Part A: Polymer Chemistry, vol. 45, 2007, pp. 3150-3165.

Robert T. Mathers, et al.: "Synthesis and Polymerization of Renewable 1,3-Cyclohexadiene Using Metathesis, Isomerization, and Cascade Reactions with Late-metal Catalysts", Macromolecular Rapid Communication, 2011, 32, pp. 1338-1342.

(Continued)

*Primary Examiner* — Ling Choi
*Assistant Examiner* — Chun-Cheng Wang
(74) *Attorney, Agent, or Firm* — McDermott Will & Emery LLP

(57) ABSTRACT

The preparation of cyclohexadienes from one or more plant oils is disclosed. The cyclohexadiene can be used to form polymers or derivatized to form other monomers that can be used to form polymeric materials.

16 Claims, 4 Drawing Sheets

(56) References Cited

OTHER PUBLICATIONS

Robert T. Mathers: "How Well Can Renewable Resources Mimic Commodity Monomers and Polymers?", Journal of Polymer Science Part A: Polymer Chemistry, 2011, pp. 1-15.
Robert T. Mathers, et al.: "Sustainable Methods for the Synthesis and Polymerization of 1,3-Cyclohexadiene from Plant Oils", Chemical Society, Div. Fuel Chem. 2010, 55 (1).
Robert T. Mathers, et al.: "Isomerization and Polymerization of Cyclic Dienes from Plant Oils", Polymer Preprint, ACS meeting San Diego, Sep. 29, 2011, p. 1.
Robert T. Mathers: Abstract, Warwick Polymers Conference, Abstract Book, MacroGroup UK International Conference on Polymer Synthesis & UKPCF International Conference on Polymer Colloids, Warwick Polymers, Jul. 9-12, 2012, pp. 1-2.
Miaton et al.: Green Chemistry, vol. 12, No. 10, Oct. 2010, pp. 1677-1872.
Laurant Mailon, et al.: "Polyalkylenehydroxybenzoates (PAHBs): Biorenewable Aromatic/Aliphatic Polyesters from Lignin", Macromolecular Rapid Communications, 2011, 32, pp. 1386-1392.
Kozo Tanaka, et al.: "Characterization of solid superbases prepared from y-alumina and their catalytic activity", Applied Surface Science 121/122, 1997, pp. 461-467.
Robert T. Mathers: "Sustainable Methods for the Synthesis and Polymerization of 1,3-Cyclohexadiene from Plant Oils", *Prep. Pap.-Am. Chem. Soc., Div. Fuel Chem.* 2011, 56 (2), 91.

* cited by examiner

PLANT BASED MONOMERS AND POLYMERS

CROSS-REFERENCE TO RELATED APPLICATION

This application claims the benefit of U.S. Provisional Application No. 61/654,589 filed Jun. 1, 2012, the entire disclosure of which is hereby incorporated by reference herein.

TECHNICAL FIELD

The present disclosure relates to plant based monomers and polymers. In particular, the present disclosure describes the preparation of cyclohexadiene monomers and derivatives thereof from plant oils and polymers therefrom.

BACKGROUND

Petroleum-based aromatic monomers are widely used to prepare polymeric materials. Such monomers include terephthalic acid, styrene, divinyl benzene, bisphenol A, phenylene diamine, and phthalic anhydride. Since the rigidity and stability of the aromatic ring provides good thermal and mechanical properties, a wide variety of thermoplastic and thermoset materials have utilized these types of monomers For example, terephthalic acid is a well known commodity monomer that finds widespread use by the plastics industry for the synthesis of films, fibers, and bottles made with polyethylene terephthalate (PET). Other polymers, such as Kevlar, also utilize petroleum-based terephthalic acid or derivatives of terephthalic acid.

The consumption of terephthalic acid, which is often referred to as purified terephthalic acid (PTA), and the corresponding dimethyl ester of PTA are approximately 9 billion lbs per year. (Wittcoff, H. A.; Reuben, B. G.; Plotkin, J. S. *Industrial Organic Chemicals*; Wiley: Hoboken, N.J., 2004.) The synthesis of PTA is based on petroleum derived paraxylene. The subsequent copolymerization of PTA with ethylene glycol, which is based on petroleum derived ethylene, yields polyethylene terephthalate (PET).

There has been an effort to produce terephthalic acid using biobased technology. One approach involves converting glucose-derived isobutanol to para-xylene from a corn-based platform. Subsequently, the para-xylene is converted to terephthalic acid. Another approach involves preparing terephthalic acid from a biomass containing a terpene or terpenoid, such as limonene. See, e.g., U.S. Patent Publication No. 20100168461.

However, more effective methods for preparing monomers and polymers based on plants or biomass are still desired. In addition, there is a desire to develop processes and products from renewable sources that can substitute or supplement petroleum-based chemicals.

SUMMARY OF THE DISCLOSURE

An advantage of the present invention is a process for preparing monomers from one or more plant oils. The monomers derived from the one or more plant oils can be used to form polymers or used in other reactions to form other compounds including other monomers.

These and other advantages are satisfied, at least in part, by a process for preparing cyclohexadiene. The process comprises contacting an oil derived from a plant with a metathesis catalyst to produce 1,4-cyclohexadiene and residual plant oil and separating the 1,4-cyclohexadiene from the residual plant oil. Advantageously, the 1,4-cyclohexadiene can be converted to other monomers including 1,3-cyclohexadiene through an isomerization reaction. In addition, either the 1,4-cyclohexadiene and the 1,3-cyclohexadiene can be converted to a PTA mimic, e.g., saturated and unsaturated bicyclic monomers, e.g., bicyclic anhydrides, diesters, diacids, and monocyclic monomers, such as monocyclic diesters and diacids.

Another aspect of the present disclosure includes processes for polymerizing the cyclohexadiene and PTA mimic thereof to polymers.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein.

DETAILED DESCRIPTION OF THE DISCLOSURE

Figure 1:
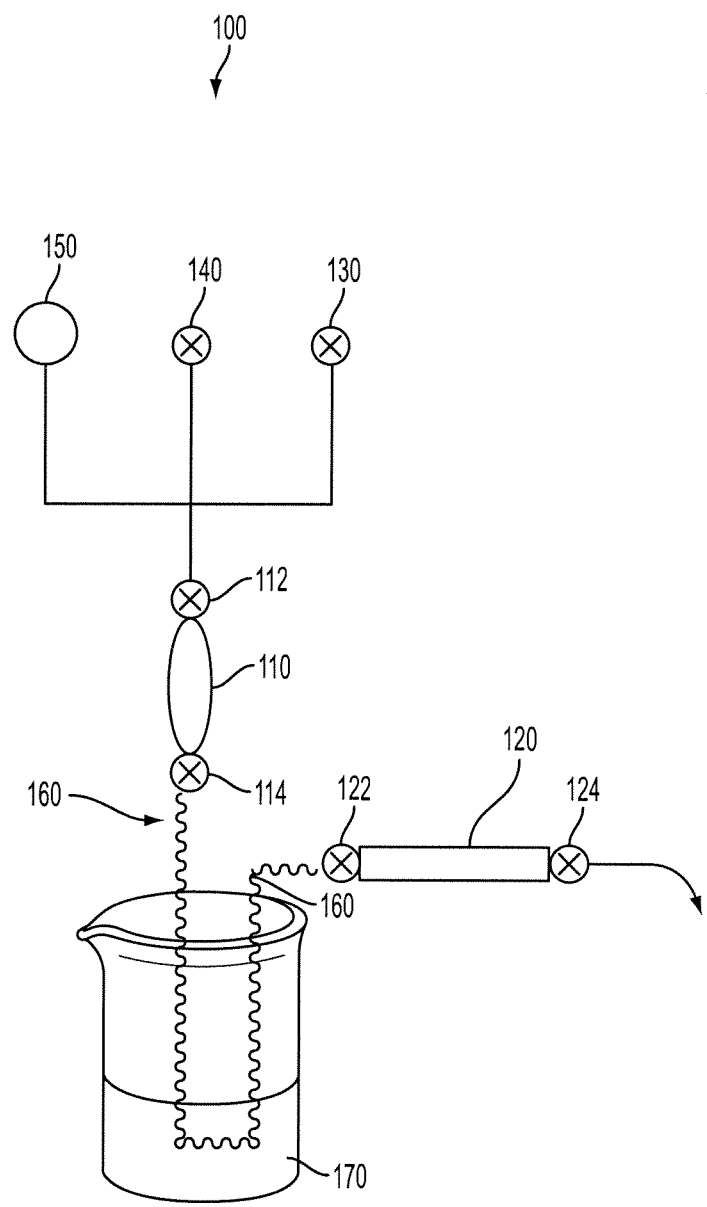
FIG. 1 is schematic illustration of a continuous flow reactor for the isomerization of 1,4-CHD to 1,3-CHD.

The present disclosure describes the preparation of plant-based monomers that can be used per se or the plant-based monomers can be derivatized to other monomers or compounds. Such monomers can then be used to supplement or substitute monomers traditionally used in the preparation of polymeric materials. The preparation methods described herein can be advantageously performed with little to no plant oil purification, minimal catalyst loading, no organic solvents, and simple product recovery by distillation.

In one aspect of the present disclosure, a process for preparing cyclohexadiene is disclosed. The process comprises contacting an oil derived from a plant with a metathesis catalyst, e.g., a ruthenium catalyst, to produce 1,4-cyclohexadiene and residual plant oil. The 1,4-cyclohexadiene can then be separated from the reaction mixture, e.g. residual oil and/or catalyst, and isomerized to 1,3-cyclohexadiene. The 1,3-cyclohexadiene can then be derivatized to other compounds including other monomers, such as a PTA mimic, and/or polymerized either alone or with other monomers to form one or more polymers therefrom.

The plant oil that can be used in the present disclosure include one or more oils derived from soybean, corn, canola, linseed, rapeseed, coconut, palm, sunflower, peanut, cottonseed, etc. Preferably the plant oil contains polyunsaturated triglycerides. The oil can be derived from any part of the plant such as the seed of the plant. Oils or mixtures of oils with polyunsaturated fractions are feasible as well as the methyl and ethyl esters of these plant oils. Advantageously, the plant oil does not need further purification from the type of plant oil currently available from commercial sources.

The monomer of 1,3-cyclohexadiene (1,3-CHD) has found widespread use in polymer chemistry and Diels-Alder reactions. Strategies for polymerizing 1,3-CHD involve anionic, cationic and free-radical mechanisms, as well as polymerizations conducted with rare-earth and transition metal catalysts. Much of the interest in polycyclohexadiene (polyCHD) stems from the excellent physical properties that cyclic monomers impart to polymers and the ability to transform polyCHD into conducting polymers and proton conductors.

Numerous synthetic methods have been reported for the synthesis of 1,3-CHD that utilize dehydrohalogenation, dehydration, and oxidation reactions. In comparison, reduction reactions of benzene usually produce 1,4-CHD. Examples of starting materials for the synthesis of 1,3-CHD include 1,2-dibromocyclohexane, bromocyclohexene, chlorocyclohexene, cyclohexenol, allylic phosphites, allyl ethers, 1,2-cyclohexane diol, cyclohexane, and cyclohexene. From a green chemistry standpoint, producing 1,3-CHD with elimination reactions generates larger quantities of waste and utilizes stoichiometric reagents compared to catalytic reactions.

The present disclosure, in contrast, describes an economical alternative to petroleum-based options which uses metathesis and alkene isomerization reactions to prepare useful monomers. In addition, the monomers can be readily polymerized alone or with other monomers to form polymers.

For example and as shown in Scheme 1a, several commercially available plant oils were examined as a source of renewable 1,4-cyclohexadiene (1,4-CHD). These plant oils were chosen because they contain polyunsaturated triglycerides that could react with a metathesis catalyst and generate volatile diene products suitable for distillation. The second generation ruthenium metathesis catalyst ([triglyceride]/[catalyst] approximately 5000) dissolved readily in neat plant oil and allowed high turnover numbers. Other metathesis catalysts, such as $WCl_6/(CH_3)_4Sn$ have been shown to produce 1,4-CHD from methyl linoleate and methyl linolenate using [linoleate]/[$WCl_6$] ratios of approximately 12 and 32.

Scheme 1. Synthesis of renewable starting materials using a) plant oils to produce 1,4-CHD, b) isomerization of 1,4-CHD to 1,3-CHD and c) one-pot isomerization and polymerization cascade sequence with a nickel (II) acetylacetonate/methaluminoxane (MAO) catalyst.

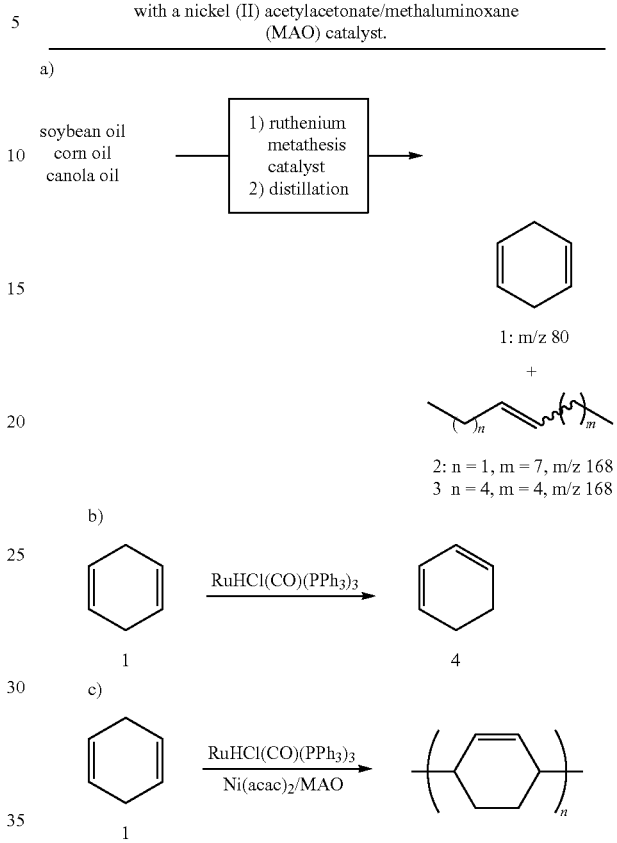

Based on known values for the polyunsaturated fraction, the maximum estimated yield of 1,4-CHD would be expected to decrease as follows: linseed (64 mol %, 17.8 wt. %)>soybean (34 mol %, 9.5 wt. %)>corn (28 mol %, 7.8 wt. %)>canola/rapeseed (22 mol %, 6.2 wt. %)>coconut (1.6 mol %, 0.4 wt %) and palm kernel oil (1.5 mol %, 0.4 wt. %). Since experimental results for soybean oil (500 g) produced larger amounts of 1,4-CHD (7.1 wt. %) than corn oil (6.6 wt. %) and canola oil (5 wt. %), soybean oil was selected as the most economical alternative to linseed oil. The yields in Scheme 1a are modest, but despite the limitations presented by the polyunsaturated fraction, triglycerides offer a sustainable alternative to the Birch reduction of benzene and other elimination reactions which produce halogenated waste. In addition, Scheme 1a was easily scaled-up to 800 g reactions in common 1 L round-bottom flasks and 1500 g in 2 L round-bottom flasks. From a green chemistry standpoint, the experimental design requires no purification of the plant oils, minimal catalyst loading (1 mg catalyst/5 g plant oil), no organic solvents, and simple product recovery by vacuum distillation. The residual plant oil, which becomes cross-linked after the metathesis reaction, can be utilized for other purposes.

After recovery of the metathesis products, 1,4-CHD (1) (m/z 80) was detected by GC/MS. $^1H$ NMR confirmed resonances for 1,4-CHD at δ 2.7 (—$CH_2$—) and δ 5.7 (=CH—) ppm. Under the conditions examined in Scheme 1a, the unsaturated triglycerides also resulted in the formation of dodecene (2, 3) isomers (19%, m/z 168). The methyl groups for these isomers were detected by $^1H$ NMR at δ 0.85 and δ 0.77 ppm.

For purposes related to polymer chemistry, Scheme 1a would be more useful if 1,4-CHD was isomerized to 1,3-CHD (Scheme 1b). Numerous catalysts facilitate the conjugation of diener and some of these are based on rhodium, platinum, ruthenium, titanium, zirconium, and iron. One particular catalyst, based on a ruthenium hydride (RuH), has been reported for the isomerization of acyclic dienes, 1-hexene and unsaturated esters. Since this ruthenium catalyst [RuHCl(CO)(PPh$_3$)$_3$] was successful with acyclic dienes, the complex was extended to 1,4-CHD. After preparing the catalyst from ruthenium(III) chloride, triphenylphosphine (TPP) and formaldehyde, FTIR analysis confirmed the RuH absorbance at 2014 cm$^{-1}$ ($v_{RuH}$) as well as the CO absorbances at 1904 cm$^{-1}$ ($v_{CO}$), and 1922 cm$^{-1}$ ($v_{CO}$). Comparison of a phenyl C—H absorbance for neat TPP (3066 cm$^-$) with the RuH catalyst ($v_{RuTPP}$=3059 cm$^{-1}$) and other TPP bearing complexes, such as Wilkinson's catalyst (ClRh(PPh$_3$)$_3$) ($v_{RhTPP}$=3058 cm$^{-1}$), confirmed that coordination of TPP to the metal center shifted the TPP absorbance to lower wavenumbers.

The isomerization of neat 1,4-CHD in Scheme 1b was conducted under nitrogen for 1 h at 85° C. with [1,4-CHD]/[RuH] ratios as high as 5000. The FTIR absorbance at 3026 cm$^{-1}$ for 1,4-CHD decreased and a new absorbance at 3037 cm$^{-1}$ appeared for the 1,3-CHD. Formation of 1,3-CHD was also accompanied by the appearance of a strong bending absorbance at 655 cm$^{-1}$ ($v_{=CH-}$) for the conjugated diene. As the isomerization progressed, GC detected a decrease in 1,4-CHD combined with a increase in a new peak for 1,3-CHD. The formation of benzene was minimal and amounted to 1-2% for reaction temperatures between 60-85° C.

The conversion of 1,4-CHD to 1,3-CHD under Scheme 1b was typically 65-70% and was independent of catalyst loading ([1,4-CHD]/[RuH]=1000-5000), time (1-24 h), and temperature (60-95° C.). Since the RuH catalyst gives yields as high as 95% for acyclic dienes, the reaction yields in Scheme 1b are not a consequence of catalyst activity. Rather, acyclic dienes conjugate more readily than 1,4-CHD due to small differences in thermodynamic stability between 1,4- and 1,3-CHD isomers. In fact, acid-catalyzed hydration experiments and heats of hydrogenation confirm the dienes in 1,3-CHD do not benefit from the stability afforded to other conjugated dienes, such as those found in 1,3-cycloheptadiene and 1,3-cyclooctadiene. If the difference in stability for 1,3-CHD and 1,4-CHD was larger, then higher yields would be possible. Entering the reported ΔG values of 1.7-2.4 kJ/mol into equation 1 (R=8.31 J mol$^{-1}$ K$^{-1}$), puts the isomerization in perspective and suggests the maximum yields for an equilibrium process in Scheme 1b would be 65-70%.

$$\Delta G = -RT \ln K \tag{1}$$

The polymerization in Scheme 1c was examined as a one-step cascade and compared with a two-step sequential isomerization-polymerization. Since the desired yield for Scheme 1b was limited by the small ΔG differences between 1,3- and 1,4-CHD, the current system would be best suited for catalysts that are able to selectively polymerize 1,3-CHD in the presence of 1,4-CHD. As a result, a polymerization was examined with transition metal catalyst systems rather than alkyllithium initiated anionic polymerizations which are known to undergo chain transfer with 1,4-CHD. This does not necessarily mean that anionic polymerizations of 1,3-CHD derived from plant oils would not produce polymers, but the molecular weights would be reduced in the presence of chain transfer agents such as 1,4-CHD. Early transition metal catalysts, such as Et(Ind)$_2$ZrCl$_2$, Me$_2$Si(Ind)$_2$ZrCl$_2$ and Cp$_2$ZrCl$_2$, provided minimal polymerization activity (<4 kg polymer mol$^{-1}$ h$^{-1}$) when activated with methaluminoxane (MAO) ([Al]/[Zr]=2000) at ambient temperature in toluene for 3 h. Since late-metal catalysts were much more active for this system, polymerizing renewable polyCHD with a nickel (II) catalyst is the focus of this polymerization section.

When activated by MAO, nickel(II)acetylacetonate (Ni(acac)$_2$) will polymerize styrene, 1,3-butadiene, and 1,3-CHD. In Table 1, the polymerization of renewable 1,3-CHD (4) was successful even in the presence of 1,4-CHD (1) and dodecene isomers (2-3). Initially, sequential two-step isomerization-polymerizations were examined in hydrogenated d-limonene (entry 1), toluene (entry 2), and neat monomer (entry 3). Hydrogenated d-limonene is a non-petroleum polymerization solvent that has been reported for metallocene polymerizations and ROMP. The polymerization activity increased with increases in (1,3-CHD), the (Al)/(Ni) ratio, and the temperature. Comparison of the two-step method (entry 4) with a one-step isomerization-polymerization cascade (entry 5) indicated that the two-step method gave higher yields because the 1 h isomerization period in entry 4 facilitated a much larger (1,3-CHD) value in the initial stage of the polymerization. Since the one-pot cascade reaction involves a simultaneous isomerization and polymerization, control experiments established that RuHCl(CO)(TPP)$_3$ does not polymerize 1,3-CHD in the presence of MAO but the MAO slows down the isomerization reaction.

TABLE 1

Polymerization of renewable 1,3-CHD (4) with Ni(acac)$_2$/MAO catalyst.[a]

| Entry | Method[b] | Catalyst | Solvent[c] | [4]$_o$[d] (M) | Time[e] (min) | Temp (° C.) | (Al)/(Ni) | Yield (g) | Activity (kg mol$^{-1}$ h$^{-1}$) | T$_d$ (° C.)[f] | T$_m$ (° C.)[g] |
|---|---|---|---|---|---|---|---|---|---|---|---|
| 1 | 2-step | Ni(acac)$_2$ | h-dL | 0.6 | 30 | 23 | 1000 | 0.200 | 40 | 305 | 293 |
| 2 | 2-step | Ni(acac)$_2$ | toluene | 0.8 | 30 | 23 | 1000 | 0.626 | 125 | 327 | 322 |
| 3 | 2-step | Ni(acac)$_2$ | neat | 4.9 | 30 | 23 | 100 | 0.202 | 40 | 329 | 316 |
| 4 | 2-step | Ni(acac)$_2$ | neat | 4.9 | 30 | 90 | 100 | 0.226 | 45 | 327 | 311 |
| 5 | cascade | Ni(acac)$_2$ | neat | 0 | 30 | 90 | 100 | 0.050 | 10 | 325 | 274 |
| 6 | cascade | Ni(acac)$_2$ | neat | 0 | 90 | 90 | 100 | 0.053 | 4 | 320 | 274 |
| 7 | 2-step | Ni(acac)$_2$/2P(tol)$_3$ | neat | 5.0 | 30 | 23 | 100 | 0.050 | 10 | 326 | 312 |
| 8 | 2-step | Ni(acac)$_2$/P(tol)$_3$ | neat | 5.0 | 30 | 90 | 100 | 0.206 | 41 | 326 | 308 |

TABLE 1-continued

Polymerization of renewable 1,3-CHD (4) with Ni(acac)$_2$/MAO catalyst.[a]

| Entry | Method[b] | Catalyst | Solvent[c] | [4]$_o$[d] (M) | Time[e] (min) | Temp (° C.) | (Al)/(Ni) | Yield (g) | Activity (kg mol$^{-1}$ h$^{-1}$) | $T_d$ (° C.)[f] | $T_m$ (° C.)[g] |
|---|---|---|---|---|---|---|---|---|---|---|---|
| 9 | 2-step | Ni(acac)$_2$/ P(tol)$_3$ | h-dL | 1.3 | 90 | 90 | 100 | 0.170 | 11 | 326 | 309 |

[a]Polymerizations run with 0.01 mmol catalyst, solid MAO, and 4 mL of 1-4 such that (1,3-CHD)/(Ni)~2000.
[b]2-step sequence involved isomerization for 1 h at 85° C. followed by polymerization. Cascade method involved a simultaneous isomerization-polymerization.
[c]h-dL = hydrogenated d-limonene.
[d]Initial (1,3-CHD) calculated by determining the conversion in Scheme 1b using GC. For cascade polymerizations, initial (1,3-CHD) = 0 and initial (1,4-CHD)/(Ni) ratio~3000.
[e]Polymerization time does not include a 1 h isomerization period for 2-step reactions.
[f]Onset of decomposition ($T_d$) measured by thermogravimetric analysis (TGA) under nitrogen at 10° C./min.
[g]Melting point ($T_m$) measured by differential scanning calorimetry (DSC) under nitrogen at 10° C./min.

The polymerization of 1,3-CHD with Ni(acac)$_2$ in toluene produces highly crystalline polyCHD ($T_m$=320-328° C.) that is primarily composed of 1,4-linkages. In Table 1, the polymerization of renewable 1,3-CHD in toluene resulted in $T_m$ values as high as 322° C. In addition, FTIR spectroscopy of the polyCHD identified absorbances at 3027 cm$^{-1}$ (=CH— st) and 747 cm$^{-1}$ (=CH—) for the cis alkene in the 1,4-linkages. Glass transition temperatures were not detectable by differential scanning calorimetry (10° C./min) on the first or second heating cycles. Because the $T_m$ values in entry 2 were close to the onset of decomposition ($T_d$), lowering the $T_m$ values or widening the gap between $T_m$ and $T_d$ to create a melt-processable polymer would be advantageous. As a result, the influence of several experimental parameters on the $T_m$ values was investigated. In entries 1-3, decreasing the solvent polarity and [1,3-CHD] decreased $T_m$ values by 29° C. Increasing the temperature (entry 4) also decreased the stereoregularity of the polymer and the resulting $T_m$ value. The cascade isomerization-polymerizations (entries 5-6) resulted in the lowest $T_m$ values and may be attributed to the low [1,3-CHD] values during the polymerization. Since triphenylphosphine and tricyclohexanephosphine are reported to alter the isotactic diads during styrene polymerizations with nickel(II) catalysts, the influence of Lewis bases on the $T_m$ values was also considered. In entries 7-9, the presence of tri(o-tolyl)phosphine gave small decreases in $T_m$ values. The solvent polarity in entry 9 is also expected to lower the $T_m$ values. A comparison of entries 3 and 7 indicated tri(o-tolyl) phosphine reduced the polymerization activity at ambient temperatures. As a result, it is believed that the use of phosphine bases may be more suited for higher temperatures (entries 8-9).

In another aspect of the present disclosure, the 1,4-CHD compound derived from plant oil is used to construct numerous analogues that mimic the structure and physical properties of PTA. Such compounds are referred to herein as PTA mimics and include, for example saturated and unsaturated bicyclic monomers, e.g., bicyclic anhydrides, diesters, diacids, and monocyclic monomers, such as monocyclic diesters and diacids. Scheme 2 illustrates example pathways to first form 1,4-CHD and then convert 1,4-CHD to one or more PTA mimics.

Scheme 2. Overview for utilizing soybean oil for the synthesis of PTA mimics.

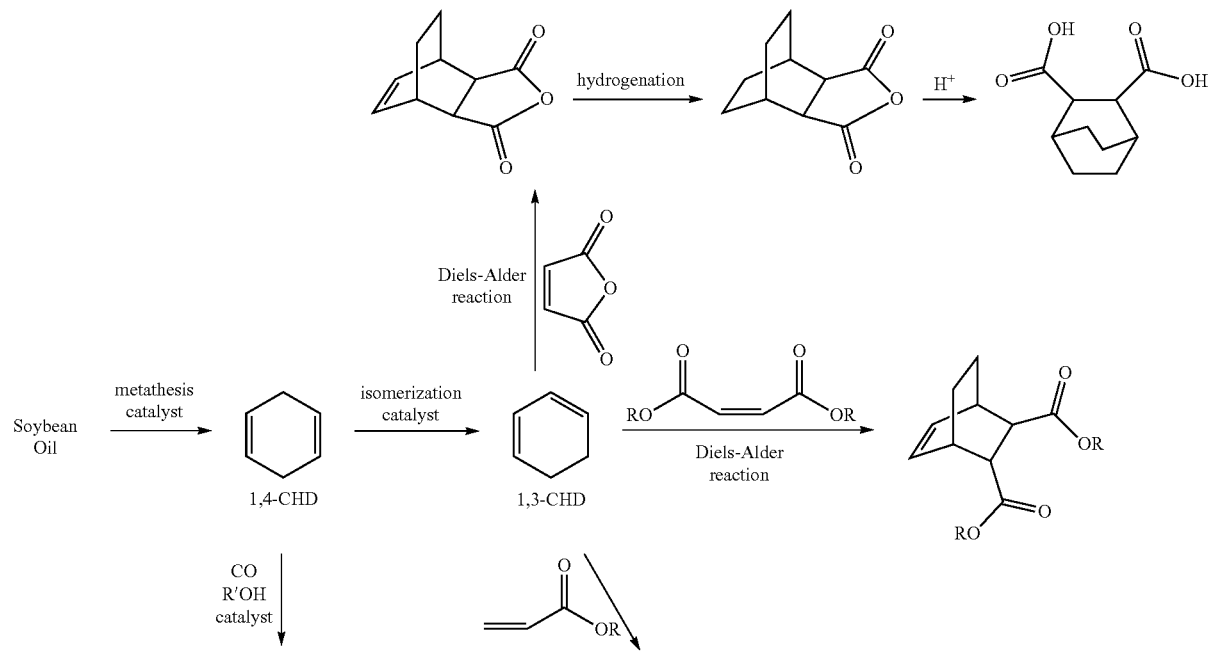

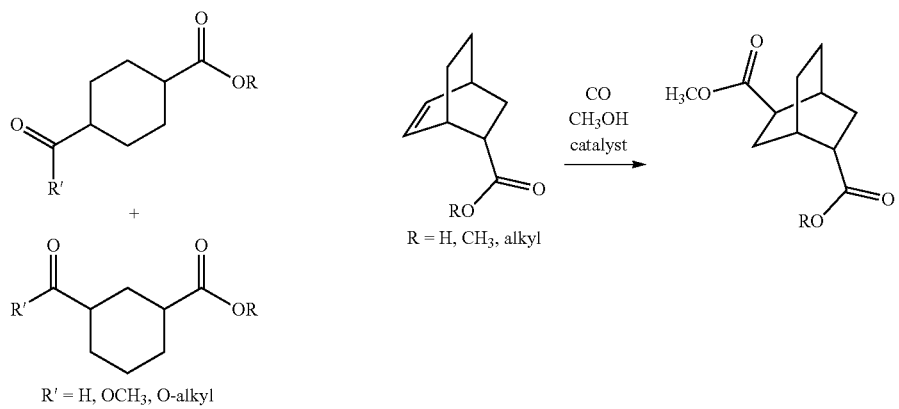

R = H, CH₃, alkyl

R' = H, OCH₃, O-alkyl

One approach for optimizing the preparation of 1,4-Cyclohexadiene includes starting with modified plant oils. For example, during the formation of 1,4-CHD, the monounsaturated fraction of soybean oil also reacts and produces a viscous oil. The viscosity of the oil necessitates the use of a vacuum pump to distill the resulting 1,4-CHD in a reasonable time period. Although PTA derivatives using unmodified soybean oil can be made, starting with the methyl or ethyl esters of soybean oil, such as is the case with biodiesel, would allow the concomitant synthesis of 1,4-CHD and difunctional esters. These long chain aliphatic diesters have lower viscosity than the cross linked soybean oil and will decrease the time needed for distillation and recovery of 1,4-CHD. Additionally, these long chain aliphatic diesters can increase the economic viability of the process by reducing the amount of waste and serving as monomers for other types of polymers.

As shown in Scheme 2, both isomers of cyclohexadiene (1,4-CHD and 1,3-CHB) allow the synthesis of analogues of PTA via Diels-Alder reactions and carbonylation chemistry. Diels-Alder reactions give high yields, do not require a catalyst, and will occur at ambient temperatures. The substrates for the Diels-Alder reactions, such as anhydrides (i.e. maleic anhydride), esters (ie. methyl acrylate), and diesters (ie. dimethyl maleate and dimethyl fumarate), have been chosen since they are readily availability and economical. Existing carbonylation catalysts, such as $Co_2(CO)_8$, can be optimized for this system. The formation of cyclic and bicyclic rings after Diels-Alder reactions will provide monomers and polymers therefrom with a range of thermal stability and physical properties.

In one aspect of the present disclosure, monomers prepared from plant oil can be polymerized alone or converted to another monomer such as a PTA mimic. The PTA mimic monomer can be polymerized with other monomers, such as by condensation reactions with diamines and/or diols for example. In addition, unsaturated alcohols such as 2-hydroxyethyl methacrylate (HEMA) can also be used in forming monomers derived from plant oil. Such monomers could then be free radically polymerized or photopolymerized. The preparation of the monomers derived from plan oil and subsequent polymerization of the monomers can be done in separate steps or in a combine of steps.

For example, in an effort to reduce the number of synthetic steps, produce less chemical waste, and potentially simplify the monomer purification, cascade reactions as illustrated in Scheme 3 can be undertaken. Experiments to combine the isomerization of 1,4-CHD and the Diels-Alder reaction in a one-pot reaction have been successful. It is preferable that the catalyst in the cascade reactions only performs isomerization and does not react with maleic anhydride or dimethyl maleate. The ruthenium catalyst of $RuHCl(CO)(TPP)_3$ is such a catalyst that can be used as an isomerization catalyst that tolerates functional group such as the carbonyl groups in maleic anhydride.

Scheme 3. The synthesis of polyesters and polyamides using cascade reactions to minimize the number of synthetic steps during the monomer synthesis.

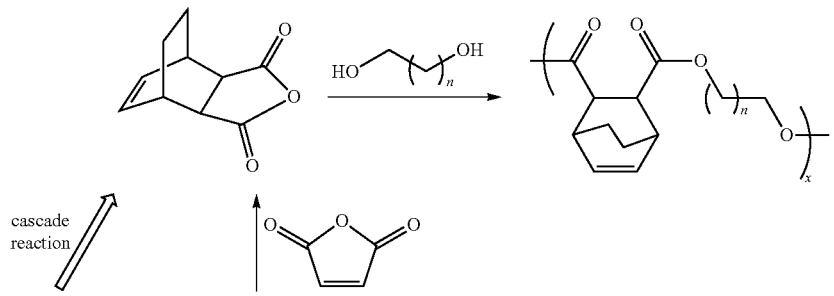

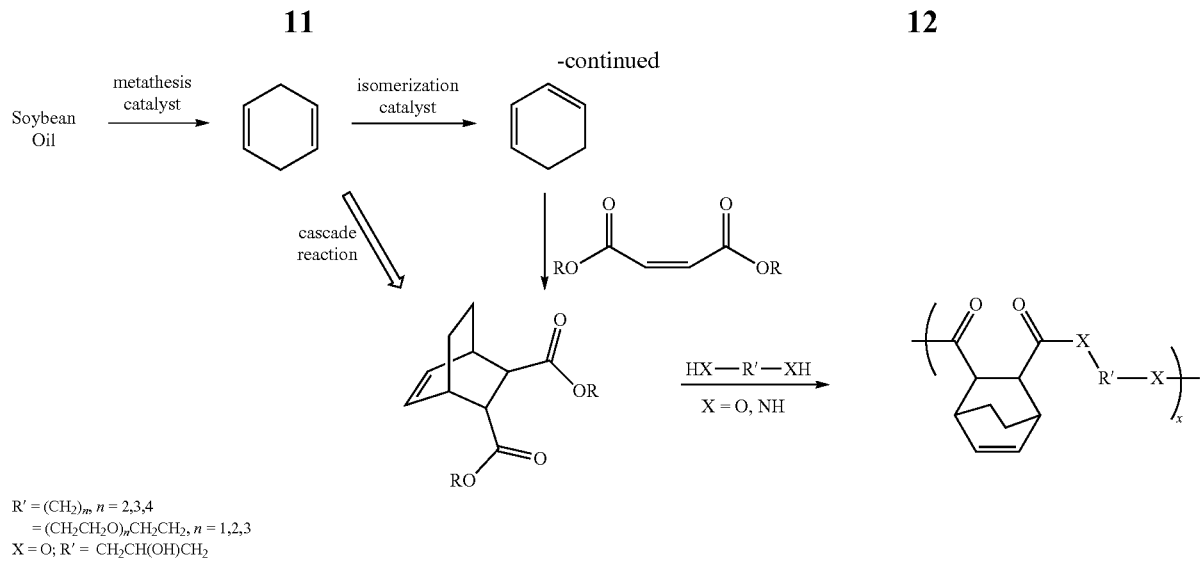

R' = (CH$_2$)$_n$, n = 2,3,4
   = (CH$_2$CH$_2$O)$_n$CH$_2$CH$_2$, n = 1,2,3
X = O; R' = CH$_2$CH(OH)CH$_2$

As shown in Scheme 3, bicyclic and monocyclic monomers can be prepared from plant oil. The monomers prepared from plant oil can be polymerized, such as by condensation reactions with diamines and/or diols for example. The diols useful for polymerizing the monomers obtained from plant oil can include one or more petroleum based diols; one or more dilos derived from fatty acids, such those from oleic acid, linoleic acid, ricinoleic acid, etc.; one or more bio-based diols, e.g., 1,3-propanediol (1,3-PDO), 1,4-butanediol (1,4-BDO); and one or more substituted diols such as glycerol.

Bicyclic monomers are highly desirable for reasons related to physical properties and optical clarity. It is believed that the thermal stability of the monomer and the resulting polyesters and polyamides in Scheme 4 will improve after the alkenes which result from the Diels-Alder reactions undergo hydrogenation or carbonylation reactions. Hydrogenations will result from treating alkene containing monomers with low to moderate pressures of hydrogen gas (i.e. 1-50 psi) in the presence of heterogeneous catalysts such as 5 Pd or Pt on carbon. The hydrogenation can easily be monitored by observing the decrease in FTIR absorbance for the alkene CH stretch at about 3158 cm$^{-1}$. The carbonylation of alkenes in 1,4-CHD and 1,3-CHD in the presence of alcohols or diols will produce esters functionalities.

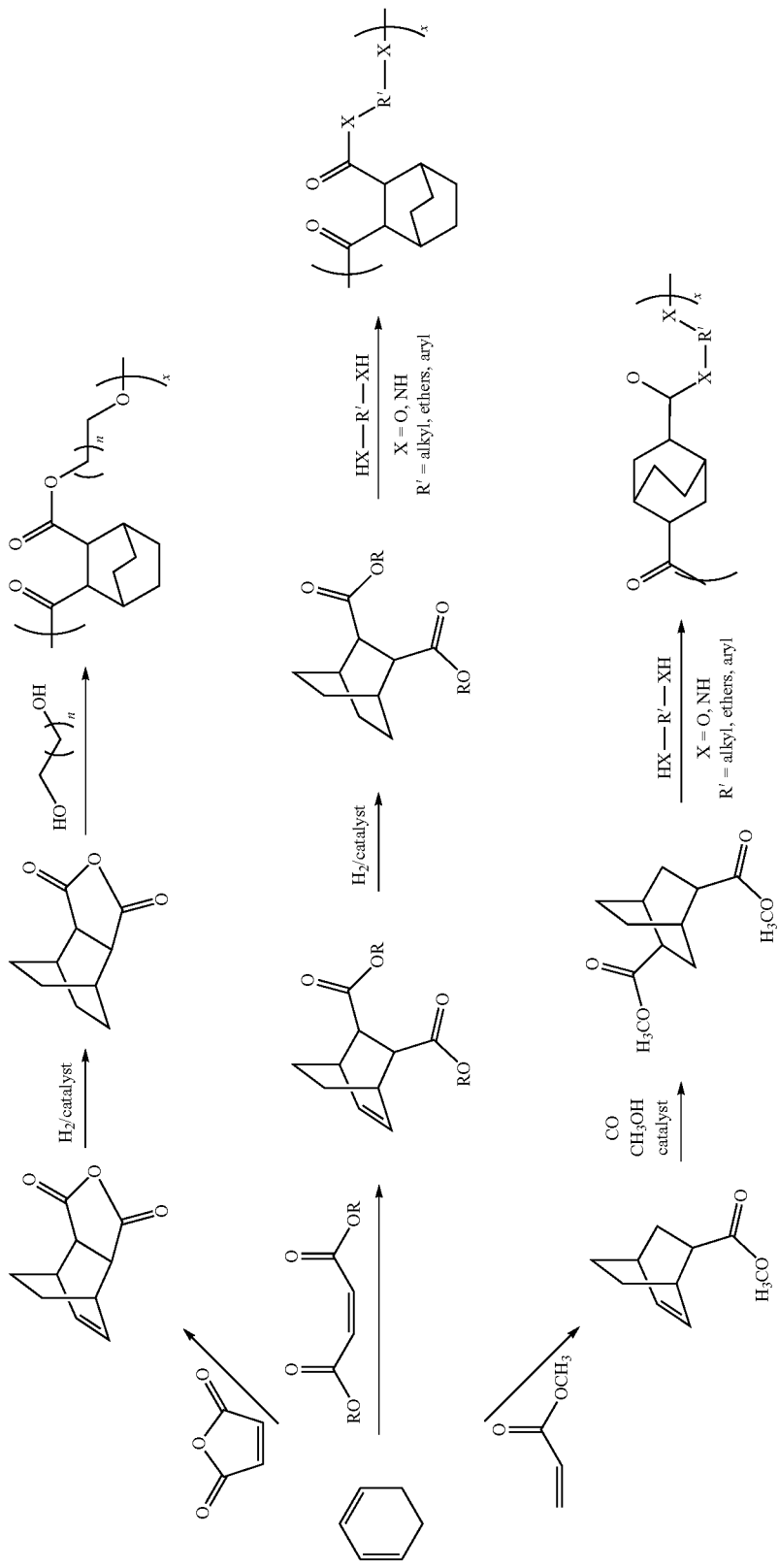

In another aspect of the present disclosure, 1,4-CHD can be isomerized with solid bases including metal oxides and alkali metals. It is generally known that isomerization of certain alkenes can be performed with solid bases such as metal oxides ($Na_2O$, $K_2O$, CaO, MgO, and $ZrO_2$) in combination with small amounts of alkali metals, such as sodium and potassium. The resulting metal oxides are highly basic and have been described as superbases (pKa>26). See, e.g., G. Busca, Chem. Rev., 2010, 110, 2217-2249. However, there does not appear any report of isomerizing 1,4-CHD with a solid base.

Hence, in addition to homogeneous batch processes of isomerizing 1,4-CHD to 1,3-CHD with ruthenium complexes, a reusable heterogeneous catalyst can be used to isomerize 1,4-CHD to 1,3-CHD and facilitate a subsequent Diels-Alder reaction to prepare PTA mimics in a single, and continuous step. This continuous process can be carried out as one-pot cycloaddition reaction that is easily scalable while replacing transition metal catalysts with a recyclable solid base containing highly abundant and non-toxic elements. These solid bases can be formed by combining metal oxides, such as $Na_2O$, $K_2O$, CaO, MgO, $ZrO_2$, $MoO_3$, $TiO_2$, etc. and mixed metal oxides with small amounts of alkali metals, such as sodium and potassium. Solid bases that can be used in the present disclosure can be prepared, for example, by first calcination of a support (usually gamma-$Al_2O_3$, MgO, or CaO) at temperatures above about 400-500° C. Addition of alkali metal hydroxide (NaOH or KOH) can then be added to the support and may involve lower temperatures, e.g., around 300-400° C. An alkali hydroxide, e.g., NaOH, can be added in stages while stirring and heating. Usually, a flow of nitrogen is used to remove water. Then the alkali metal (Na or K) will be added. Alkaline-earth metal carbonates and alkali carbonates (Na2CO3) may also serve as a source of metal.

One-Pot Monomer Synthesis

As depicted in Scheme 5, a cyclic diene (1,4-CHD) which can be prepared from the polyunsaturated fraction of soybean oil was isomerized and transformed into bicyclic-anhydride monomers 5 and 6. In order to create a one-pot synthesis procedure, the catalytic isomerization was conducted as a continuous process in a continuous flow reactor. Such a reactor is depicted in FIG. 1. As shown in the figure, continuous flow reactor 100 includes reservoir 110 in fluid connection to catalyst chamber 120. Reservoir 110 includes gas inlet 130 which allows gas, e.g., nitrogen or other inert gas, to pressurize reservoir 110 which contains the 1,4-CHD and causes the 1,4-CHD in reservoir 110 to flow to catalyst chamber 120 which contains a solid base catalyst. Reservoir 110 also includes valves 112 and 114 for isolating the reservoir and is also connected to valve 140 which allows additional 1,4-CHD into the reservoir and pressure gage 150 for determining the pressure in the reservoir. Catalyst chamber 120 can be configured to more readily transfer heat such that the temperature of the chamber can be readily controlled (temperature control not shown for illustrative convenience) and can include vales 122 and 124 to isolate the chamber. In this example, reservoir 110 is connected to catalyst chamber 120 through coil 160, which can be surrounded, in part, by heat exchanger 170 for cooling the 1,4-CHD being transferred from reservoir 110 to catalyst chamber 120. Flow reactor 100 can be made of materials that do not significantly react or interfere with the reactions contemplated for the reactor, e.g., stainless steel. After passing through catalyst chamber 120, 1,4-CHD can be isomerized and outputted to another reaction system or isolated. Hence, through the use of a flow reactor, such as shown in FIG. 1, 1,4-CHD can be continuously isomerized to 1,3-CHD and available for further reactions, e.g., a Diels-Alder reaction with maleic anhydride.

Scheme 5. One-pot synthesis of bicyclic-anhydride 5 and 6 using renewable 1,4-cyclohexadiene.

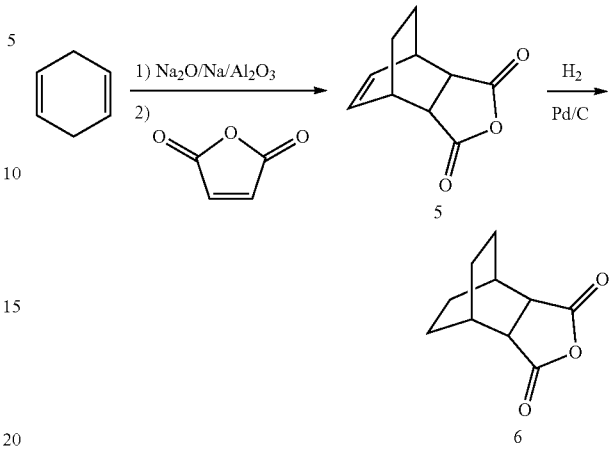

Figure 2:
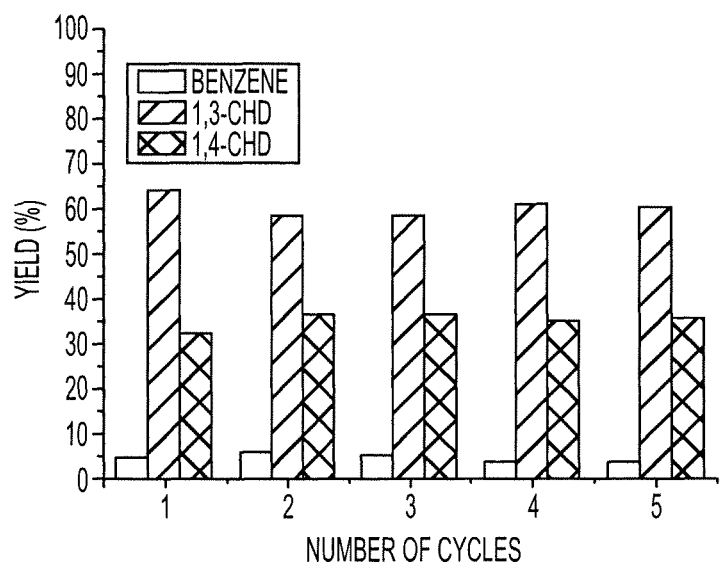
FIG. 2 is chart showing the results of recycling $Na/Na_2O$ catalyst that was used for the isomerization of 1,4-CHD to 1,3-CHD.
Figure 3:
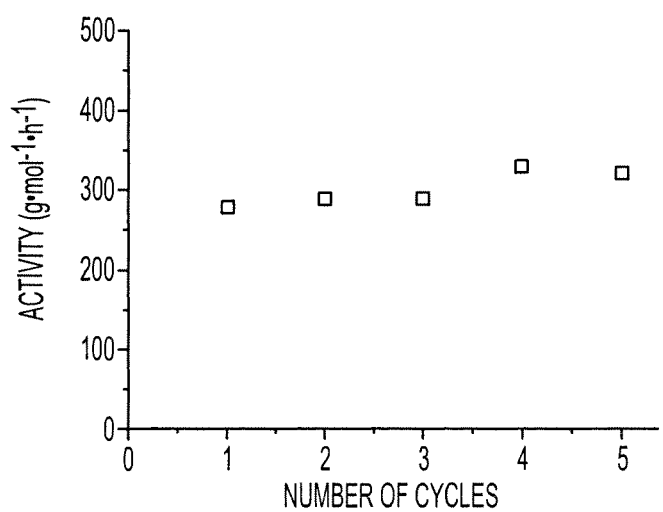
FIG. 3 is chart showing the results of recycling $Na_2O$ catalyst that was used for isomerization of 1,4-CHD under continuous flow conditions.

In operation, the flow reactor as depicted in FIG. 1, for example, can pressurize the reservoir with an inert gas, i.e., nitrogen to about 10-20 psi to flush 1,4-CHD from the reservoir through a temperature controlled catalyst chamber, e.g., catalyst column, containing a supported isomerization catalyst based on Na/$Na_2O$. In this example, the reservoir holds approximately 100 mL of 1,4-CHD. Depending on the pressure, the flow rate could be varied between 1-5 mL/min. The isomerization was easily scalable and allowed the $Na_2O$ catalyst to be recycled numerous times (see FIGS. 2 and 3), e.g., greater than 5 cycles with at least 250 g $mol^{-1}$ $h^{-1}$ of catalyst activity. In fact, loss in catalyst activity after 5-10 trials only occurred if protic impurities, such as water, were present in the 1,4-CHD.

It is believed that the accepted mechanism for isomerization of alkenes with solid bases occurs via an allylic deprotonation mechanism. Although this mechanism can require high temperatures (300° C.) for 1-butene and MgO, more reactive catalysts will isomerize substituted alkenes at lower temperatures. For example, Na/NaOH on γ-$Al_2O_3$ isomerizes β-pinene and 5-vinylbicyclo[2.2.1]hept-2-ene at 25° C. and 20° C., respectively. See H. Gorzawski and W. F. Hoelderich, *Journal of Molecular Catalysis A: Chemical*, 1999, 144, 181-187; K. Tanaka, H. Yanashima, M. Minobe and G. Suzukamo, *Applied Surface Science*, 1997, 121-122, 461-467. It is believed that because the two alkenes on 1,4-CHD enhance the acidity of the allylic hydrogens, facile deprotonation and generation of a stable anion occurs. Based on temperature studies from 0 C to 25 C, the isomerization process in Scheme 5 operates efficiently at about 0° C. In addition, the continuous flow of 1,4-CHD through the catalyst bed minimized the exothermic reduction of 1,4-CHD to benzene which predominately occurred above 20° C.

After flushing 1,4-CHD through the isomerization reactor and onto solid maleic anhydride (MA), a Diels-Alder reaction was conducted at moderate temperatures (e.g., 60° C. was the most common temperature, but 40-80° C. can also be used) without organic solvent. MA was chosen since the Diels-Alder reaction exhibits a high degree of reactivity without a catalyst, allows easy product recovery via crystallization, and can be derived from biomass using furfural, 5-hydroxyfurfural or 1-butanol. In effect, a renewable source of maleic anhydride advantageously allows mimicking terephthalic acid and phthalic anhydride with 100% renewable carbon content. Previously, achieving polyesters that are 100% renewable has been challenging and often requires an aromatic monomer derived from petroleum. Therefore, this approach provides a process that allows current systems based on isosorbide, linseed oil, or malonate derivatives of fatty methyl esters.

Diels-Alder experiments with a slight excess of 1,3-CHD, gave 85-90% yield after 3 h for temperatures between 40-60° C. Upon cooling to room temperature, unreacted 1,3-CHD is recycled under reduced pressure before recrystallizing the product. Based on $^1$H NMR, LC/MS, FTIR, and DSC, detectable amounts of MA were not present in the product after recrystallization with ethanol. The predominately endo product was confirmed by high resolution LC/MS (m/z 179.07023, error −0.27 ppm). Additionally, the alkene in 5 was detected by $^1$H NMR (δ 6.34 ppm), $^{13}$C NMR (δ 133.05 ppm), and FTIR (3055 cm$^{-1}$). Characterization of 5 by DSC detected a large endotherm at 115° C. for the endo product and a smaller endotherm for the exo product at 149° C. As determined by FTIR, $^1$H NMR, LC/MS (m/z 181.08590, error −0.115 ppm) quantitative hydrogenation of 5 was achieved. $^1$H NMR spectroscopy indicated disappearance of alkene resonance at δ 6.34 ppm, while the anhydride remained unchanged.

Polymerization with Renewable Diols

In another aspect of the present disclosure, 100% renewable polyesters can be prepared from either PTA mimic monomers 5 and 6, which were derived from plant oil, and one or more bio-based diols, e.g., 1,3-propanediol (1,3-PDO), 1,4-butanediol (1,4-BDO) and glycerol. See Scheme 6. The copolymerization of a diol, e.g., (1,4-BDO), and glycerol with monomers 5 or 6 would also be beneficial for manipulating the physical properties of the resultant polymer. In addition, unsaturated alcohols such as 2-hydroxyethyl methacrylate (HEMA) can also be used in forming monomers that could then be free radically polymerized or photopolymerized.

Figure 4:
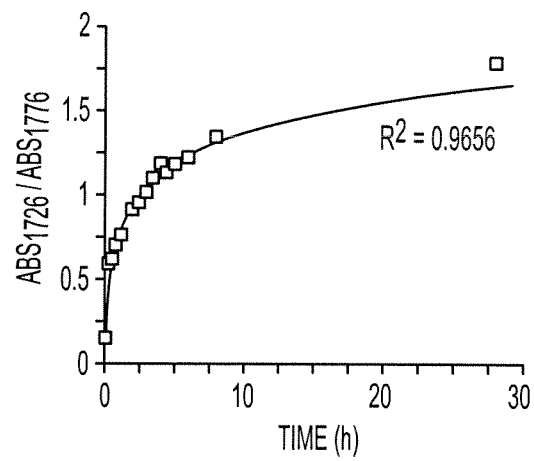
FIG. 4 is a chart showing FTIR spectroscopy data for the polymerization of 1,4-BDO and 5 ([1,4-BDO]/[5]=1) at 100° C. with para-toluenesulfonic acid (PTSA).

As shown in Table 2 and FIG. 4, the progress of these solvent-free polymerizations was conveniently monitored by FTIR spectroscopy by comparing the anhydride absorbance (1776 cm$^{-1}$) of the monomer with the carbonyl stretch of the polyester (1726 cm$^{-1}$). FIG. 4 is a chart showing FTIR spectroscopy data for the polymerization of 1,4-BDO and 5 ([1, 4-BDO]/[5]=1) at 100° C. with p-toluenesulfonic acid (PTSA). Zinc acetate, zinc chloride, and Ti(OBu)$_4$ will also work as catalyst for this reaction. FIG. 4 shows that the progress of the polymerization can be followed by FTIR spectroscopy. As Abs$_{1726}$/Abs$_{1776}$ increased with time for the polyesters, GPC confirmed an increase in the weight-average (M$_w$) molecular weight and intrinsic viscosity ([η]). Among the alcohols, glycerol afforded higher molecular weights compared to polyesters derived from the 1,3-PDO and 1,4-BDO.

Scheme 6. Polycondensation of anhydride 6 and glycerol using a catalyst.

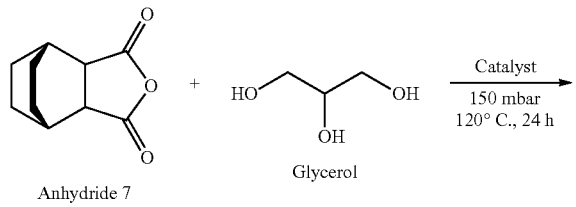

Anhydride 7

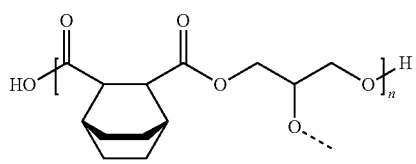

The chemical shifts and relative integrations in $^1$H and $^{13}$C NMR spectra confirmed results from FTIR (FIG. 4) and indicated formation of the anticipated polyester microstructure. $^{13}$C NMR analysis of the polymerization of 5 with glycerol detected carbonyl resonances for ester groups involving the primary alcohol on glycerol (δ 174.78 ppm) as well as the secondary alcohol on glycerol (δ 174.50 ppm). These carbonyl resonances were distinct compared to monomer (δ 173.98 ppm) and carboxylic acid (δ 178.08 ppm) terminated polyesters. Since both the primary and secondary alcohols on glycerol participate in the polymerization, a hyperbranched structure is expected. GPC measurements of the Mark Houwink exponent (a=0.33-0.48) in FIG. 5 also suggested a hyperbranched structure that was consistent with an AB$_2$ type monomer, such as glycerol. The results of the polymerization of anhydride 7 with different diols are provided in Table 2.

TABLE 2

Polymerization of anhydride 7 with different diols.$^a$

| Entry | Monomers | M$_w$ (g/mol)$^b$ | M$_w$/M$_n$$^b$ | [η]$^b$ (mL/g) | Abs$_{1726}$/ Abs$_{1776}$$^c$ | T$_g$$^d$ (° C.) | T$_d$$^e$ (° C.) |
|---|---|---|---|---|---|---|---|
| 1 | 1,3-PDO | 2200 | 2.7 | 3.1 | 1.2 | -nd- | 160 |
| 2 | 1,4-BDO | 8730 | 1.4 | 6.8 | 1.9 | 13 | 185 |
| 3 | glycerol | 9350 | 2.2 | 6.7 | 10 | 57 | 286 |

$^a$Polymerizations were conducted at 120° C. for 24 h under dynamic vacuum (150 mbar).
$^b$Measured by GPC in THF at 35° C. using light scattering and viscometer detectors.
$^c$Absorbance ratios of ester (1726 cm$^{-1}$) and anhydride (1776 cm$^{-1}$) peaks determined by FTIR spectroscopy.
$^d$Measured by DSC (20° C./min) under nitrogen.
$^e$Decomposition temperature reflects 5% weight loss as measured by TGA (20° C./min) under nitrogen.

In Table 3, the polymerization of 7 and glycerol with a Brønsted acid (PTSA) was compared with two Lewis acids [Zn(OAc)$_2$ and Ti(OBu)$_4$]. Although PTSA gave larger FTIR absorbance ratios, higher M$_w$ values, and lower molecular weight distributions (PDI=2.2) compared to Zn(OAc)$_2$ and Ti(OBu)$_4$, all of these polyesters were below the gel point and displayed excellent solubility. One of the advantages of monomers 5 and 6 is the low melting point (FIG. S11) and high solubility of the anhydrides compared to terephthalic acid. Consequently, reasonably high M$_w$ values could be obtained after polymerizing 5 or 6 with glycerol at 120° C. after 24 h. In contrast, the high T$_m$ value of terephthalic acid (≈300° C.) renders this monomer mostly insoluble at 120° C. and prevented polymerization with glycerol from occurring.

TABLE 3

Polymerization of anhydride 7 and glycerol with different catalysts.$^a$

| Entry | Catalyst | M$_w$ (g/mol)$^b$ | M$_w$/M$_n$$^b$ | [η]$^b$ (mL/g) | Abs$_{1726}$/ Abs$_{1776}$$^c$ | T$_g$$^d$ (° C.) | T$_d$$^e$ (° C.) |
|---|---|---|---|---|---|---|---|
| 1 | none | 2560 | 2.6 | 3.0 | 1.4 | -nd- | 137 |
| 2 | Zn(OAc)$_2$ | 4960 | 5.0 | 3.1 | 1.3 | −9 | 154 |

TABLE 3-continued

Polymerization of anhydride 7 and glycerol with different catalysts.[a]

| Entry | Catalyst | $M_w$ (g/mol)[b] | $M_w/M_n$[b] | $[\eta]$[b] (mL/g) | $Abs_{1726}/Abs_{1776}$[c] | $T_g^d$ (°C.) | $T_d^e$ (°C.) |
|---|---|---|---|---|---|---|---|
| 3 | Ti(OBu)$_4$ | 5040 | 4.9 | 3.2 | 1.6 | −10 | 162 |
| 4 | PTSA | 9350 | 2.2 | 6.7 | 10 | 57 | 286 |

[a]Polymerizations conducted with catalyst (0.2 mol %) at 120° C. for 24 h under dynamic vacuum (150 mbar).
[b]Measured by GPC in THF at 35° C. using light scattering and viscometer detectors.
[c]Absorbance ratios of ester (1726 cm$^{-1}$) and anhydride (1776 cm$^{-1}$) peaks determined by FTIR spectroscopy.
[d]Determined by DSC (20° C./min). [e]$T_d$ values reflect 5% weight loss as measured by TGA (20° C./min) under nitrogen.

The thermal properties for the polyesters were determined by TGA and DSC to determine decomposition ($T_d$) and glass transition ($T_g$) temperatures. As expected, the larger $M_w$ values for entry 4 (Table 3) were also accompanied by larger $T_g$ and $T_d$ values. In contrast to the polyesters made with PTSA, the absence of a catalyst (entry 1) or the Lewis acid catalysts (entries 2 and 3) resulted in polymers with smaller $T_d$ values. Likewise, both Zn(OAc)$_2$ and Ti(OBu)$_4$ produce polymers with much lower $T_g$ values compared to PTSA ($T_g$=57° C.). The use of PTSA combined with the higher functionality of the glycerol compared to 1,4-BDO and 1,3-PDO allowed the synthesis of robust polyesters which were soluble in common organic solvents such as THF. Consequently, a Brønsted acid catalyst, such as PTSA, appears highly desirable in order to mimic the physical properties of polymers made with petroleum-based aromatic monomers.

Figure 6:
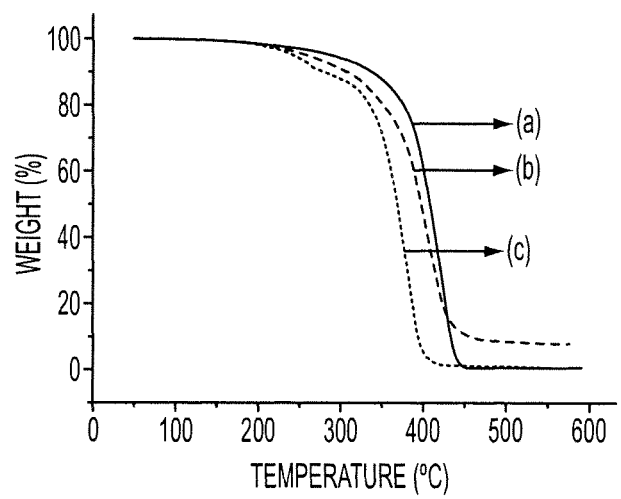
FIG. 6 represents TGA data showing comparison of decomposition temperature ($T_d$) for 5% weight loss of the polymers: (a) anhydride 6 with glycerol ($T_d$=292° C.); (b) anhydride 5 with glycerol ($T_d$=257° C.); (c) phthalic anhydride with glycerol ($T_d$=231° C.).

To show the versatility of polymerizing PTA mimic monomers 5 and 6 as a substitute to phthalic anhydride and terephthalic acid, a comparison of thermal stability was undertaken (FIG. 6). According to TGA measurements, polyesters derived from glycerol showed excellent thermal stability as evidenced by the onset of decomposition (380° C.). Interestingly, complete polymer degradation (>99%) was observed at temperature up to 600° C. (FIG. 6a). By comparison, polyesters derived from anhydride 5 ($T_d$=257° C.) and phthalic anhydride ($T_d$=231° C.) showed lower decomposition temperatures (FIGS. 4b & c). Polyesters which contain monomer 5 are slightly less thermally stable than the hydrogenated analogue (6) due to a retro Diels-Alder reaction. Since commercial PET degrades >350° C., renewable polyesters with 6 offer a better alternative to mimicking petroleum-based monomers compared to monomer 5.

Figure 5:
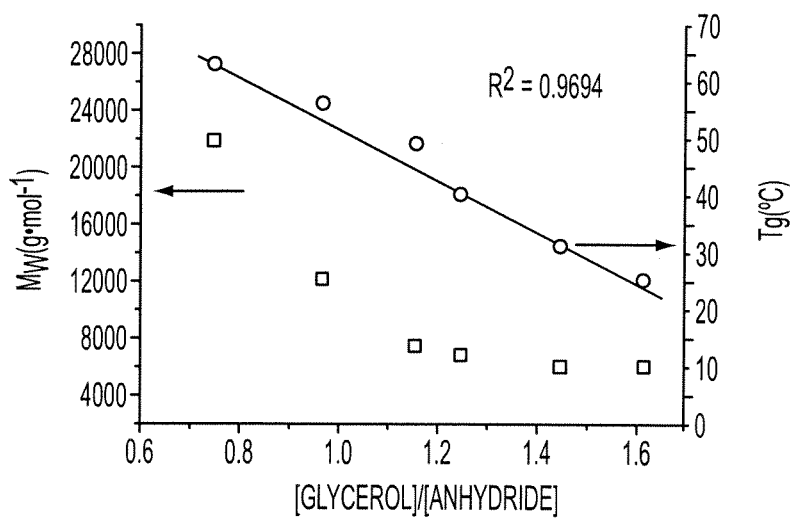
FIG. 5 is a chart showing the effect of [glycerol]/[anhydride 7] ratio on the molecular weight and glass transition temperature of polymers.
Figure 7:
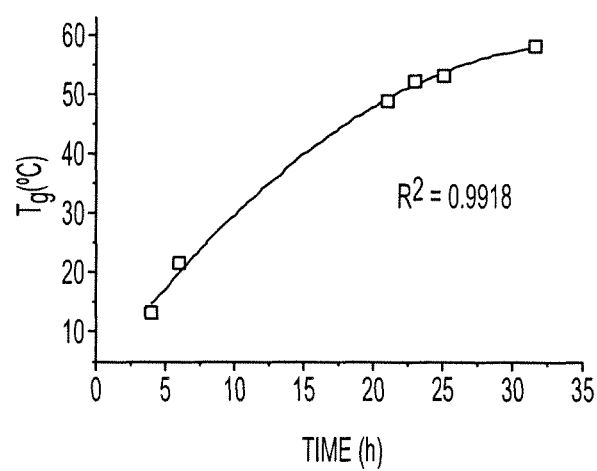
FIG. 7 is a chart showing the correlation between the glass transition temperature and the reaction time for the polymerization of glycerol with anhydride 7 ([glycerol]/[anhydride 7]=1).

Since polymerization of 7 and glycerol gave the best thermal properties, different mole ratios of anhydride 7 and glycerol were examined. As expected, different mole ratios greatly affected the physical properties of the polymers. In FIG. 5, a wide range of $M_w$ and $T_g$ (25-63° C.) values were accessible by varying the [glycerol]/[anhydride 7] ratio. Although $M_w$ and $T_g$ values were sensitive to the [glycerol]/[anhydride 7] ratio, TGA analysis indicated these polymers all exhibited similar onset of decomposition temperatures (372-380° C.). As shown in FIG. 7, kinetic studies for polymerizations with a constant mole ratio of glycerol and 7 revealed the polymer properties vary with polymerization time. For example, increasing the polymerization time increased the $M_w$ values (2620 g·mol$^{-1}$ to 13770 g·mol$^{-1}$), $[\eta]$ values (3.7 to 7.3 mL/g), and $T_g$ values (13° C. to 58° C.). Compared to $[\eta]$ values for commercial PET ($[\eta]$=−0.0147× $M_w^{0.768}$), differences are expected for the polyesters in FIG. 5.

Since glycerol has a higher functionality than the diols, crosslinked polyester thermosets are possible. A series of polymerizations were examined in order to better understand the range of physical properties which accompany thermoplastic polyesters compared to thermoset materials. Generally, thermoplastic polyesters exhibit solubility in common organic solvents, such as THF, while thermoset are insoluble. The thermoplastic polyesters displayed $T_g$ values from 13-63° C. for $M_w$ values ranging from 2500 g·mol$^{-1}$ up to 22000 g·mol$^{-1}$. At greater monomer conversion via higher catalyst loading or longer polymerization time, the functionality of glycerol allowed the synthesis of insoluble, crosslinked polymers with higher $T_g$ values (68-90° C.).

In the present disclosure, a one-pot synthesis of bicyclic monomers has been investigated as an alternative to aromatic monomers, such as terephthalic acid and phthalic anhydride. This strategy successfully transformed a waste by-product of the oleochemical industry (1,4-CHD) into bicyclic monomers. The alkene isomerization of 1,4-CHD under continuous flow is believed the first example where continuous flow transforms biomass-derived molecules to monomers. Although continuous flow processes demonstrate great utility in the hydrolysis of cellulose and the production of biofuels, it is believed that the synthesis of industrially relevant monomers via continuous flow has been unreported. Given the prevalence of alkenes in biomass, this example of a continuous flow process with a sodium oxide catalyst demonstrated a number of advantages compared to conventional batch processes with transition metal catalysts.

Polymerization of these bicyclic monomers (5 and 6) with glycerol, 1,4-BDO, and 1,3-PDO occurred at much lower temperatures (100-120° C.) compared to the typical requirements for the polymerization of terephthalic acid. These amorphous polyesters demonstrated high thermal stability and a range of $M_w$, $T_g$, and $[\eta]$ values. The [glycerol]/[anhydride] ratio was determined to be an important parameter for controlling the polyester properties.

EXAMPLES

The following examples are intended to further illustrate certain preferred embodiments of the disclosure and are not limiting in nature. Those skilled in the art will recognize, or be able to ascertain, using no more than routine experimentation, numerous equivalents to the specific substances and procedures described herein.

Materials.

Soybean oil (Wesson), canola oil (Wesson) and corn oil were purchased locally. The Grubbs 2$^{nd}$ generation ruthenium catalyst (Sigma-Aldrich) was used as received. Ruthenium (III) chloride hydrate (Strem Chemicals), formaldehyde (37 wt. % in water, Sigma-Aldrich), triphenylphosphine (99%, Sigma-Aldrich), 2-methoxyethanol (>99.0%, Sigma-Aldrich) were used as received to synthesize the RuHCl(CO)(PPh$_3$)$_3$ catalyst according to a literature procedure. The Ni(acac)$_2$ was obtained from Strem Chemicals and used as received. Methaluminoxane (PMAO-IP) was obtained from Akzo Nobel as a 13 wt % in toluene. The PMAO was dried to a powder at 80° C. for 24 h and stored in a glovebox.

Characterization.

$^1$H NMR spectra were measured with a Bruker 300 or 600 MHz NMR in CDCl$_3$ (99.8% D, Cambridge Isotope Laboratories). FTIR spectra (32 scans) were recorded with a ZnSe ATR crystal at a 4 cm$^{-1}$ resolution on a ThermoFisher Nicolet iS10 FTIR spectrometer. GC/MS analysis of 1,4-cyclohexadiene (Scheme 1a) was conducted at 10° C./min from 50° C. to 350° C. using a HP 5972 series gas chromatograph/mass spectrometer. The samples were analyzed on an Alltech AT-5 capillary column (30 m×0.25 mm i.d.×0.25 μm stationary phase thickness). GC analysis of the isomerization of 1,4- cyclohexadiene (Scheme 1b) was conducted at 5° C./min from 50° C. to 150° C. Melting point ($T_m$) and heat of fusion ($\Delta H_f$) values were determined with a TA Instruments DSC Q20 under nitrogen at 10° C./min. The decomposition temperature ($T_d$) was determined with a TA Instruments TGA Q500 at 10° C./min under a flow of nitrogen.

Synthesis of 1,4-cyclohexadiene (1).

Soybean oil was degassed and purged with nitrogen several times. The neat oil (500 g) was transferred via cannula to a flask containing a $2^{nd}$ generation ruthenium catalyst (100 mg, 0.118 mmol). The solution stirred at 60° C. while the product was distilled under reduced pressure and collected in a trap cooled with liquid nitrogen. The temperature was gradually increased to 85° C. while the distillation continued. After a total time of 48 h, 44 g of product was recovered. The product was dried with $CaCl_2$, 4 Å molecular sieves, and stored in a glovebox. $^1$H NMR (300 MHz, $CDCl_3$): δ=5.70 (s, =CH— on 1,4-CHD, 4H), 5.5-5.3 (m, =CH—, 0.44H), 2.69 (s, —$CH_2$—, 4H), 2.00 (br m, —$CH_2$—, 0.95H), 1.30 (br m, —$CH_2$, 1.73H), 0.98 (t, —$CH_3$, 0.56H), 0.90 (t, —$CH_3$, 0.74H) ppm. FTIR (ZnSe ATR) ν: 3026 (=CH—), 2991, 2959 ($CH_3$ st), 2925 ($CH_2$ st), 2882, 2858 ($CH_2$ st), 2824, 1639 (C=C st), 1462, 1430, 959 (=CH— bending), and 886 $cm^{-1}$. GC/MS m/z (min, component): 84 (2.46, 3-hexene), 84 (2.52, 3-hexene), 80 (2.68, 1,4-cyclohexadiene), 168 (5.25, dodecene), 168 (5.29, dodecene).

Isomerization of 1,4-cyclohexadiene (1) to 1,3-cyclohexadiene (4).

The $RuHCl(CO)(PPh_3)_3$ ([CHD]/[catalyst]=3000, 7.9 mg, 0.00827 mmol) was added to 1,4-CHD (3.0 mL 1-3=2.45 g 1-3=1.99 g 1=24.8 mmol 1) in a capped vial. The solution stirred under nitrogen in a sand bath at 85° C. After 1 h, the solution was cooled to ambient temperature. FTIR (ZnSe ATR) ν: 3037 $cm^{-1}$ (=CH— st), 2956, 2930, 2872, 2859 ($CH_2$ st), 2824, 1705, 1639 (C=C), 1605 (C=C), 1577, 1456, 1429, 1408, 1372, 1240, 1163, 1058, 992, 924, 886, and 655 (=CH— bending) $cm^{-1}$. GC min (abundance, component): 2.49 (2%, benzene), 2.59 (67%, 1,3-cyclohexadiene), 3.02 (31%, 1,4-cyclohexadiene).

Isomerization of 1,4-cyclohexadiene (1) and polymerization with $Ni(acac)_2$.

The $RuHCl(CO)(PPh_3)_3$ ([1,4-CHD]/[catalyst]=5000, 6.3 mg, 0.00662 mmol) was added to 1,4-CHD (4.0 mL 1-3=3.27 g 1-3=2.65 g 1=33.1 mmol 1) in a capped vial. The solution stirred under nitrogen in a sand bath at 85° C. After 1 h, the solution was cooled to ambient temperature and added to the polymerization reactor containing toluene (16 mL) and MAO (0.58 g; [Al]/[Ni]=1000). Stirred solution for 10 min before adding a solution of $Ni(acac)_2$ in toluene (4 mL). After 30 min, the catalyst was quenched with methanol (2 mL). The polymerization was vented and precipitated into acidic methanol. The polymer was filtered and washed with methanol. After drying under vacuum, 0.626 g polymer were recovered. Polymerization activity: 125 kg polymer $mol^{-1}$ $h^{-1}$. FTIR (ZnSe ATR) ν: 3027 $cm^{-1}$ (=CH— st), 2921, 2857, 1644 (C=C st), 1446, 747 (=CH—), and 726 $cm^{-1}$. TGA (10° C./min): onset=327° C. DSC (10° C./min): $T_m$=321.5, $\Delta H_f$=47.2 μg.

Diels-Alder Reactions with Maleic Anhydride.

The Diels-Alder reaction of 1,3-CHD and maleic anhydride was conducted as follows: Vials were charged with 1,4-CHD (3.2 mmol) and RuH catalyst (8 mg) in a glove box with and without toluene. Multiple reactions in various organic solvents were conducted by adding a solution of maleic anhydride (2 mmol) in either acetone, toluene, or ethyl acetate via syringe. The reactions were heated under nitrogen or argon at temperatures between ambient temperature and 90° C. for 2 to 24 h. The solvent was evaporated to obtain a solid product that was characterized by GC/MS and FTIR. The alkene in the Diels-Alder product was detected at 3058 $cm^{-1}$. The melting points varied from 134 to 142° C. depending on the amount of unreacted maleic anhydride. The presence of unreacted maleic anhydride was confirmed by the FTIR absorbance at 1776 $cm^{-1}$.

Diels-Alder Reactions with Dimethyl Maleate.

The Diels-Alder reaction of 1,3-CHD and dimethyl maleate was conducted under nitrogen. A vial containing 1,4-CHD (3.2 mmol) and RuH catalyst (8 mg) was prepared in a glovebox. The dimethyl maleate (0.288 g, 2.0 mmol) was added. The pale yellow solution was heated in the oven at 60° C. for 2 h. The initial FTIR carbonyl absorbance for the ester in dimethyl maleate (1729 $cm^{-1}$) shifted after the reaction to 1741 $cm^{-1}$. Additionally, the C=C bond in dimethyl maleate (1646 $cm^{-1}$) also shifted after the Diels-Alder reaction. These Diels-Alder reactions occur in the absence of a catalyst, but Lewis acids may facilitate higher yields or shorter reaction times.

Hydrogenation of d-limonene.

The hydrogenation of d-limonene was previously described. See Mathers, R. T.; Damodaran, K. J. Polym. Sci. Part A: Polym. Chem., 2007, 45, 3150-3165 for more detail.

Additional Materials for Use with One-Pot Monomer Synthesis and Polymerization with Renewable Diols.

1,4-Cyclohexadiene (synthesized from soybean oil by metathesis), $Na_2O/Na/Al_2O_3$ (11.5-13.5% $Na_{2O}$, 1.8-3.0% Na, Strem Chemicals), maleic anhydride (99%, Acros), palladium on carbon (10 wt %, Sigma-Aldrich), 1,3-propanediol (98%, Sigma-Aldrich), 1,4-butanediol (>99%. Sigma-Aldrich), glycerol (>99.5%, Sigma-Aldrich), p-toluenesulfonic acid (PTSA) (97.5%, Acros), zinc acetate dihydrate (98%, Acros), $Ti(OBu)_4$ (97%, Sigma-Aldrich). All polymerizations were performed in vials which were heated in a customized multi-well aluminum reactor under dynamic vacuum (150 mbar).

Characterization for One-Pot Monomer Synthesis and Polymerization with Renewable Diols.

The $^1$H and $^{13}$C NMR spectra were measured at ambient temperature using Bruker Avance 700 MHz NMR in $CDCl_3$ (99.8% D, Cambridge Isotope Laboratories). FTIR spectra (32 scans) were recorded with a ZnSe ATR crystal at a 4 $cm^{-1}$ resolution on a ThermoFisher Nicolet iS10 FTIR spectrometer. GC analysis of the isomerization of 1,4-cyclohexadiene was conducted under isothermal conditions at 50° C. with helium using thermal conductivity detector.

Molecular weights of the polymers were determined by gel permeation chromatography (GPC). The GPC system was equipped with a three-angle Wyatt MiniDawn light scattering detector (λ=690 nm, 30 mW GaAs laser), a Wyatt ViscoStar viscometer and a Wyatt OptiLab ReX differential refractometer. The light scattering detector was calibrated with the known Rayleigh ratio for toluene. The specific refractive increments (dn/dc) were calculated with Wyatt Technology's Astra V software assuming 100% mass recovery of the injected polymers. Two columns (PL gel, 5 μm MIXED-C linear, 300 mm×7.5 mm) contained 5 μm particles with pore sizes ranging from 50 to $10^6$ Å were heated at 35° C. and eluted with tetrahydrofuran (1.0 mL/min). The polymers solutions (200 μL) in tetrahydrofuran (THF) were injected at a concentration of 10-15 mg/mL.

Glass transition ($T_g$) temperatures of the polymers were determined with a TA instruments Q20 differential scanning calorimeter (DSC) at a heating rate of 20° C./min under nitrogen flow (20 mL/min). The reported $T_g$ values were taken as the midpoint of transition from the second heating cycle. The decomposition temperature ($T_d$) was determined with a TA Instruments TGA Q500 at 20° C./min under nitrogen.

Liquid chromatography/mass spectrometry (LC/MS) data was obtained by injecting a 1 µL aliquot into a Waters Acquity UPLC in line with a Thermo Scientific LTQ-Orbitrap in ESI (+) mode. The UPLC system was equipped with a BEH phenyl column (130 Å, 1.7 µM, 2.1 mm×75 mm) equilibrated in 95% solvent A (0.1% formic acid) and 5% solvent B (0.1% formic acid in acetonitrile) at 0.400 mL/min. Mass spectra data were collected using full Fourier transform mode with 30000 resolution. The mass spectra across all peaks were averaged, and the neutral mass spectrum was extracted using the associated Thermo Scientific Qual Browser 2.0.7 SP1 software.

General Procedure for Isomerization with Solid Base.

A customized isomerization reactor was built with stainless steel Swagelok components. The reactor included a reservoir for 1,4-CHD, a catalyst tube, a connection for nitrogen. The catalyst tube was loaded in a glove box with solid base catalyst and attached to the reactor. The 1,4-CHD was flushed through the temperature controlled catalyst under nitrogen pressure. The isomerization was repeated with a different cycle using the same catalyst by flushing 1,4-CHD. The samples were analyzed by GC chromatography and FTIR spectroscopy. GC/Retention time min (component, %): 2.14 (benzene, 3.9%), 2.21 (1,3-CHD, 63.8%), 2.55 (1,4-CHD, 32.3%). FTIR IR: 3090 cm$^{-1}$ and 3071 cm$^{-1}$ (=C—H stretching, benzene), 3036 cm$^{-1}$ (=C—H stretching, 1,3-CHD), 2925 cm$^{-1}$ (—CH— stretching, 1,3-CHD), 1813 cm$^{-1}$ (CH$_2$ wagging), 1478 cm$^{-1}$ (—CH— bending 1,3-CHD), 1035 cm$^{-1}$, 977 cm$^{-1}$ (—CH— out of plane bending).

Synthesis of Anhydride 5 from 1,3-CHD and Maleic anhydride.

1,3-Cyclohexadiene (36.40 g, 0.4543 mol) and maleic anhydride (29.10 g, 0.2968 mol) were charged to a 250 mL Schlenk flask containing a magnetic stir bar. The Schlenk flask was then fitted with a condenser and placed under dynamic nitrogen after which the flask was heated to 60° C. Within five minutes of heating all of the maleic anhydride had dissolved to form a bright yellow colored solution with concomitant refluxing of 1,3-cyclohexadiene followed by subsequent solidification of the charge to light yellow colored crystals within 25 minutes following the beginning of heating. The reaction was allowed to continue for a total of three hours after which unreacted 1,3-cyclohexadiene was removed via reduced pressure. Crystalline yellow solid was then recrystallized from 200 proof ethanol and the Diels Alder adduct 5 was obtained as a crystalline white solid 46.54 g (88% yield). $^1$H NMR (700 MHz, CDCl$_3$, 25° C.): δ=1.43 (d, J=7.7 Hz, 2H, CH$_2$ cyclohexene), 1.62 (d, J=7.7 Hz, 2H, CH$_2$ cyclohexene), 3.15 (t, 2H, —CH—CO)), 3.25 (m, 2H, methine cyclohexene), 6.33 (dd, J=7.7 Hz, 4.2 Hz, 3.5 Hz, 2H, —CH=CH—). $^{13}$C NMR (700 MHz, CDCl$_3$, 25° C.): δ=22.98 (CH$_2$, cyclohexene), 31.63 (methine cyclohexene), 44.77 (—CH—CO), 133.05 (—C=C—), 172.83 (CO). IR: 3055 cm$^{-1}$ (=C—H stretching), 2980-2870 cm$^{-1}$ (CH stretching), 1867-1766 cm$^{-1}$ (C=O stretching), 1462-1322 cm$^{-1}$ (CH bending), 1238-1177 cm$^{-1}$ (C—O stretching), 1075-684 cm$^{-1}$ (CH out of plane bending). LC-MS: m/z 179.07 (M$^+$), 151.07, 147, 133, 123, 105, 79, 73.

Synthesis of Anhydride 6 from the Hydrogenation of Anhydride 5.

Diels Alder adduct (Anhydride 1) (9.269 g, 0.05202 moles) dissolved in 100 mL ethyl acetate and 5 wt % Palladium on carbon (0.250 g) were added in Fisher porter bottle and purged with nitrogen. The reactor was then charged with H$_2$ (20 psi) and allowed to stir at room temperature while monitoring the reaction pressure. When the reaction pressure had dropped to 5 psi the system was recharged with H$_2$ (20 psi) and the process repeated over a period of 1 day until consumption H$_2$ had ceased. The reaction mixture was centrifuged and the product mixture isolated by decantation. The spent Pd/C catalyst was washed (twice) with 25 mL aliquots of ethyl acetate and all filtrate portions combined and reduced to a solid under dynamic vacuum at room temperature to yield an off-white powder of Anhydride 2, 8.91 g (95.0% yield). $^1$H NMR (700 MHz, CDCl$_3$, 25° C.): δ=1.58 (s, 4H, CH$_2$ cyclohexane), 1.62 (dd, J=7.7 Hz, 2H, CH$_2$ cyclohexane), 1.74 (dd, J=7.7 Hz, 2H, CH$_2$ cyclohexane), 2.24-2.26 (m, 2H, —CH— cyclohexane), 3.12 (dd, J=3.5 Hz, 2.1 Hz, 2H, —CH—CO). $^{13}$C NMR (700 MHz, CDCl$_3$, 25° C.): δ=21.37 (CH$_2$ cyclohexane), 24.12 (CH$_2$ cyclohexane), 25.98 (methine cyclohexane), 44.25 (—CH—CO) 173.98 (CO). IR: 2946 cm$^{-1}$, 2875 cm$^{-1}$ (CH stretching), 1858-1745 cm$^{-1}$ (C=O stretching), 1480-1316 cm$^{-1}$ (CH bending), 1273-1196 cm$^{-1}$ (C—O stretching), 1076-700 cm$^{-1}$ (CH out of plane bending). LC-MS: m/z 181.08 (M$^+$), 167, 153, 139, 135, 107, 79.

General Polymer Synthesis with Renewable Diol Procedure.

In a typical polymerization, a magnetically stirred reaction vial was charged with monomers (Anhydride/diols) and catalyst (PTSA/Zn(OAc)$_2$/Ti(OBu)$_4$) and heated at 120° C. in a customized multi-well aluminum reactor with constant stirring (250 rpm) until the monomer melts. After 15 min, the solution becomes clear and the polymerization was continued under dynamic vacuum (150 mbar) at 120° C. until the required polymerization time. The polymer was then characterized by FTIR, GPC, NMR, DSC, and TGA.

Polymerization of Anhydride and Glycerol with PTSA.

Anhydride monomer (0.35 g, 2 mmol), glycerol (0.18 g, 2 mmol) and PTSA (0.7 mg, 0.004 mmol) was charged in a magnetically stirred reaction vial and heated at 120° C. in a customized multi-well aluminum reactor with constant stirring (250 rpm) until the monomer melts. After 15 min, the polymerization was continued under vacuum (150 mbar) at 120° C. for a period of 27 h. The polymerization progress was deduced from the FTIR spectra using a ratio of absorbances which corresponded to the starting monomer anhydride (1776 cm$^{-1}$) and the polymer (1726 cm$^{-1}$). GPC (in THF): M$_w$=12050 g/mol, M$_w$/M$_n$=2.43, [η]=7.1 mL/g. $^1$H NMR (700 MHz, CDCl$_3$, 25° C.): 1.45 (singlet broad, 4H, CH$_2$ cyclohexane), 1.53 (singlet broad, 2H, CH$_2$ cyclohexane), 1.57 (singlet broad, 2H, CH$_2$ cyclohexane), 2.07 (singlet broad, 2H, —CH— bridged), 3.04-3.12 (m, 2H, —CH—CO), 3.58-3.67 (m, 1H, —CH$_2$—CH—CH$_2$—), 3.92-4.38 (m, —CH$_2$—CH—CH$_2$—). $^{13}$C NMR (700 MHz, CDCl$_3$, 25° C.): 21.33 (CH$_2$ cyclohexane), 25.31 (CH$_2$ cyclohexane), 25.97 (CH$_2$ cyclohexane), 27.29 (—CH— cyclohexane), 43.99-44.25 (—CH—CO), 61.1 (CH$_2$—O—), 63.3 (CH$_2$—O—), 65.33 (CH$_2$—O—), 67.76 (—CH—O), 70.15 (—CH—O), 72.25 (—CH—O), 174.78 (CH$_2$—O—CO), 178 (—CH—O—CO).

TABLE 4

GC Analysis data for the isomerization of 1,4-CHD to 1,3-CHD.

| Entry | Cycles | % 1,3-CHD | %1,4-CHD | % Benzene |
|---|---|---|---|---|
| 1 | 1 | 63.8 | 32.3 | 3.9 |
| 2 | 2 | 58.4 | 36.3 | 5.3 |
| 3 | 3 | 58.6 | 36.6 | 4.8 |
| 4 | 4 | 61 | 35.3 | 3.7 |
| 5 | 5 | 60.5 | 35.7 | 3.8 |

Additional Examples Contemplated by the Disclosure

Carbonylation of 1,4-CHD and 1,3-CHD.

Alkenes, such those found in 1,4-CHD and 1,3-CHD, will undergo carbonylation (also termed hydroalkoxycarbonylation) in the presence of carbon monoxide (CO) and alcohols to yield methyl esters. These reactions involve cobalt catalysts, such as $Co_2(CO)_8$, modified with Lewis bases (ie. pyridine). The alcohol acts as a hydrogen source to yield diesters. Diols, such as ethylene glycol, 1,3-propane diol and 1,4-butane diol, may also provide a hydrogen source for the carbonylation reactions. The pressure of CO ranges from 10 to 200 bar and the reaction temperatures range from 50 to 200° C.

Polymerization of PTA Mimics with Diols.

The diesters resulting from the Diels-Alder reactions of 1,4-CHD and RuH catalyst with maleic anhydride, dimethyl maleate, or methyl acrylate are expected to polymerize with diols. The polymerizations are expected to proceed under heat and appropriate catalyst, such as titanium(IV) butoxide, titanium(IV) isoproxide, and antimony (III) oxide. Additionally, the polymerization temperature and pressure will allow removal of volatile products (ie. methanol) resulting from the condensation reactions.

Polymerization of PTA Mimics with Diamines.

The diesters resulting from the Diels-Alder reactions of 1,4-CHD and RuH catalyst with dimethyl maleate are expected to polymerize with diamines (ie. ethylene diamine). The polymerizations may not necessarily require organic solvents or the addition of a catalyst. The volatile byproducts (ie. methanol) of the reaction will be removed with a combination of heat and reduced pressure.

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A process for preparing cyclohexadiene, the process comprising:
   contacting an oil derived from a plant with a metathesis catalyst to produce 1,4-cyclohexadiene and residual plant oil;
   separating the 1,4-cyclohexadiene from the residual plant oil; and
   isomerizing the 1,4-cyclohexadiene to 1,3-cyclohexadiene.

2. The process of claim 1, further comprising derivatizing the 1,3-cyclohexadiene to a saturated or unsaturated bicyclic monomer or a saturated or unsaturated monocyclic monomer.

3. The process of claim 1, wherein the oil derived from a plant includes one or more oils derived from soybean, corn, canola, linseed, rapeseed, coconut, palm, sunflower, peanut, or cottonseed.

4. The process of claim 1, wherein the metathesis catalyst is a ruthenium metathesis catalyst.

5. The process of claim 1, comprising isomerizing the 1,4-cyclohexadiene to 1,3-cyclohexadiene by contacting the 1,4-cyclohexadiene with a solid base catalyst to form the 1,3-cyclohexadiene.

6. A process of forming a polymer, the process comprising polymerizing the saturated or unsaturated bicyclic monomer or the saturated or unsaturated monocyclic monomer prepared according to claim 2.

7. A process for preparing polymerizable monomer from plant oil, the process comprising:
   contacting an oil derived from a plant with a metathesis catalyst to produce 1,4-cyclohexadiene and residual plant oil;
   separating the 1,4-cyclohexadiene from the residual plant oil; and
   either (i) derivatizing the 1,4-cyclohexadiene to a saturated or unsaturated bicyclic monomer or a saturated or unsaturated monocyclic monomer, or (ii) isomerizing the 1,4-cyclohexadiene to 1,3-cyclohexadiene.

8. The process of claim 7, comprising derivatizing the 1,4-cyclohexadiene to a saturated or unsaturated bicyclic monomer or a saturated or unsaturated monocyclic monomer.

9. The process of claim 7, wherein the metathesis catalyst is a ruthenium metathesis catalyst.

10. A process of preparing 1,3-cyclohexadiene, the process comprising:
    contacting 1,4-cyclohexadiene with a solid base catalyst to form 1,3-cyclohexadiene.

11. The process of claim 10 further comprising converting the 1,3-cyclohexadiene to a saturated or unsaturated bicyclic monomer or a monocyclic monomer.

12. The process of claim 10, wherein the solid base catalyst includes a metal oxide and an alkali metal.

13. The process of claim 10, wherein the solid base catalyst includes one or more metal oxides selected from $Na_2O$, $K_2O$, CaO, MgO, $ZrO_2$, $MoO_3$, and $TiO_2$, combined with one or more of an alkali metal.

14. The process of claim 10, wherein the solid base catalyst is a reusable heterogeneous catalyst.

15. The process of claim 10, wherein 1,4-cyclohexadiene is converted to form 1,3-cyclohexadiene in a single, and continuous step.

16. The process of claim 11, wherein 1,4-cyclohexadiene is converted to form 1,3-cyclohexadiene and the 1,3-cyclohexadiene is converted to the saturated or unsaturated bicyclic monomer or monocyclic monomer in a single, and continuous step.

* * * * *